United States Patent [19]
Sorensen

[11] Patent Number: 5,157,192
[45] Date of Patent: Oct. 20, 1992

[54] CONVERSION OF TERTIARY ALCOHOLS TO C8+ OLEFINS

[75] Inventor: Charles M. Sorensen, Wilmington, Del.

[73] Assignee: Mobil Oil Corporation, Fairfax, Va.

[21] Appl. No.: 790,624

[22] Filed: Nov. 12, 1991

[51] Int. Cl.$^5$ .......................... C07C 1/24; C07C 11/02
[52] U.S. Cl. .................... 585/640; 585/639; 585/324
[58] Field of Search .................. 585/639, 640, 324

[56] References Cited

U.S. PATENT DOCUMENTS

| Re. 28,341 | 2/1975 | Wadlinger et al. | 208/120 |
|---|---|---|---|
| 2,636,057 | 4/1953 | Cutcher et al. | 585/640 |
| 3,308,069 | 3/1967 | Wadlinger et al. | 252/455 |
| 3,529,033 | 9/1970 | Frilette et al. | 585/640 |
| 4,343,959 | 8/1982 | Kida et al. | 585/640 |
| 4,395,580 | 7/1983 | Juguin et al. | 585/639 |
| 4,398,051 | 8/1983 | Araki et al. | 585/639 |
| 5,043,519 | 8/1991 | Orfeo et al. | 585/640 |

OTHER PUBLICATIONS

Abstract 88-52503 Japanese Patent 63101337A.
Kofke, T., et al, "A Temperature-Programmed Desorption Study of Olefin Oligomerization in H—ZSM-5", Journal of Catalysis 115, pp. 233-243 (1989).
Chang, C. D. et al., "The Conversion of Methanol and Other O-Compounds to Hydrocarbons over Zeolite Catalysts", Journal of Catalysis 47, pp. 249-259 (1977).

Primary Examiner—Anthony McFarlane
Attorney, Agent, or Firm—Alexander J. McKillop; Charles J. Speciale; Lori F. Cuomo

[57] ABSTRACT

A process for the conversion of tertiary alcohols to C8+ olefin products over a zeolite catalyst, such as zeolite Beta. The process is particularly useful for the conversion of t-butyl alcohol to 2,2,4-trimethyl pentene. A two-step partial oxidation/dimerization process to yield C8+ olefin products is also disclosed.

22 Claims, 1 Drawing Sheet

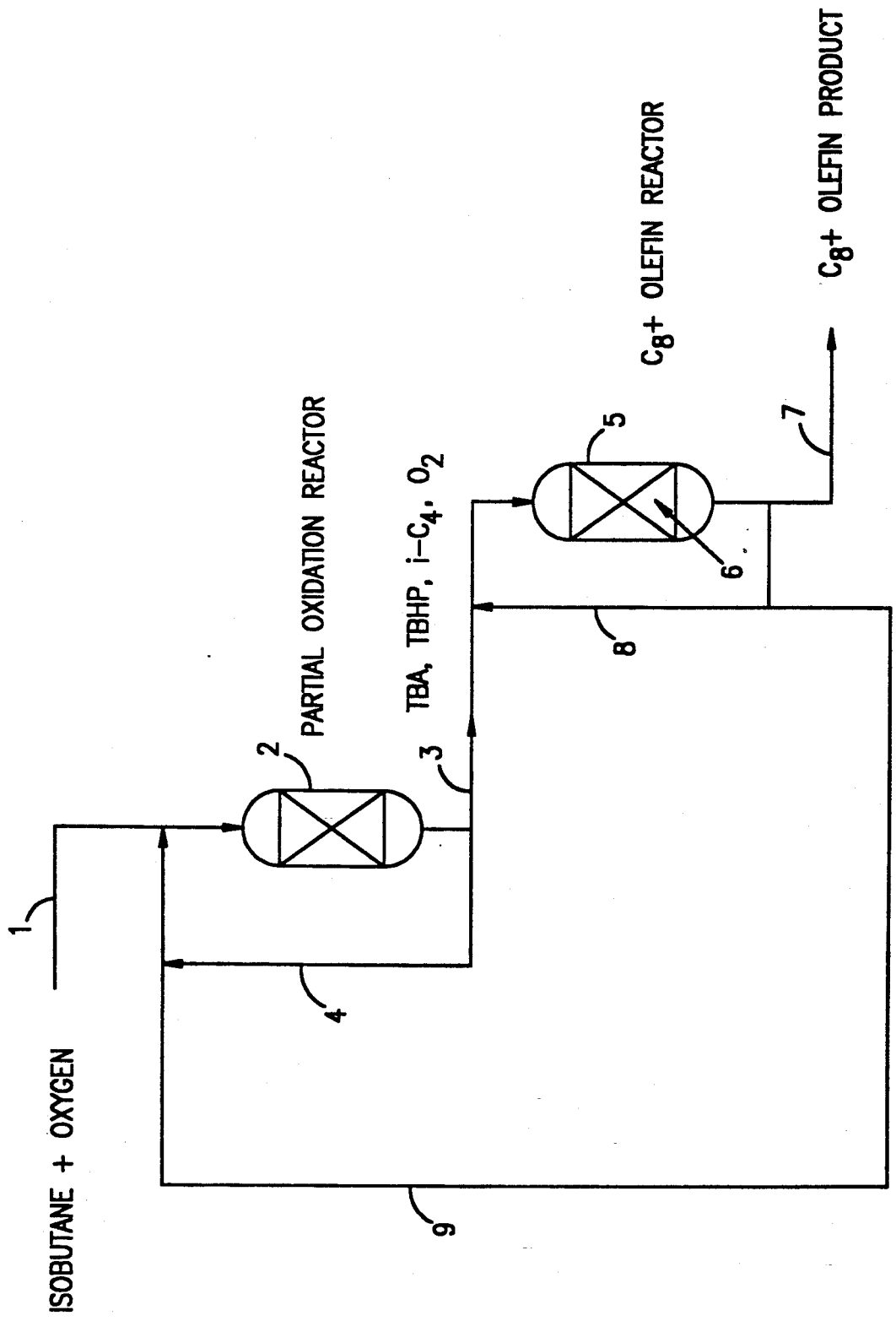

CONVERSION OF TERTIARY ALCOHOLS TO C8+ OLEFINS

FIELD OF THE INVENTION

This invention relates to a process for the conversion of tertiary alcohols to $C_8+$ olefin products over a catalyst composition comprising a large-pore, 12-membered ring material, and more particularly to a process for the conversion of t-butyl alcohol to $C_8+$ olefins over a catalyst composition comprising a zeolite having the structure of zeolite Beta.

The invention also relates to a two step process in which the tertiary alcohol is produced from the oxidation of isobutane followed by conversion over the catalyst composition comprising a large-pore, 12-membered ring material to yield $C_8+$ olefin products.

BACKGROUND OF THE INVENTION

Processes to convert alcohols to gasolines using ZSM-5 type catalysts are described in J. Catal. V. 115, N.1, p. 233-43 (1989) and J. Catal. V. 47, N.2, p. 249-59 (1977). Typical processing conditions include a temperature of about 725° F. and a pressure of about 300 psig.

Japanese Patent No. JP 6310337 teaches the use of ZSM-5 zeolite to convert TBA to isobutylene. The dehydration is carried out at a temperature of about 250°-350° F. and pressures at or above 75 psig.

It has now been found that tertiary alcohols can be converted over a catalyst composition comprising a large-pore, 12-membered ring material to give high yields of $C_8+$ olefins with very little dehydration products. Therefore, it is an object of the present invention to provide a novel process for tertiary alcohol conversion to higher octane $C_8+$ olefins. It is a further object of the present invention to provide a process for the conversion of t-butyl alcohol to $C_8+$ olefins. It is another object of the present invention for the conversion of isobutane to high octane gasoline components.

BRIEF DESCRIPTION OF THE DRAWING

The Figure is a simple schematic diagram illustrating one embodiment of the process of the present invention

SUMMARY OF THE INVENTION

The present invention provides a process for the conversion of tertiary alcohols to $C_8+$ olefins over a catalyst composition comprising a large-pore, 12-membered ring material. Moderate pressures and relatively low temperatures are important process variables that contribute to high conversion and $C_8$ olefin selectivity.

The invention therefore includes a process for the conversion of a tertiary alcohol feedstock to $C_8+$ olefins which comprises contacting said tertiary alcohol feedstock with a catalyst composition comprising a large-pore, 12-membered ring material.

The invention further includes a process for the conversion of a t-butyl alcohol feedstock to $C_8+$ olefin products which comprises contacting said t-butyl alcohol feedstock with a catalyst composition comprising a zeolite having the structure of zeolite Beta at a temperature in the range of from about 200° to about 600° F. and a pressure of greater than about 300 psig.

The invention includes in a further embodiment a process for the conversion of t-butyl alcohol to $C_8+$ olefin products which comprises:

contacting isobutane with oxygen in a first step to convert said isobutane to a partial oxidation product comprising t-butyl alcohol; and contacting said partial oxidation product comprising t-butyl alcohol with a catalyst composition comprising a large-pore, 12-membered ring material in a second step to convert said t-butyl alcohol to said $C_8+$ olefin products.

DETAILED DESCRIPTION OF THE INVENTION

The conversion catalyst of the present invention is a catalyst composition comprising a large-pore, 12-membered ring material, preferably a zeolite having the structure of zeolite Beta. Other suitable catalysts include but are not limited to zeolite Y, ZSM-20, and mordenite.

Zeolite Beta is a known zeolite, having pore windows framed by 12 tetrahedral members, and which is described in U.S. Pat. Nos. 3,308,069 and Re 28,341, incorporated herein by reference. The high selectivity for dimerization of the tertiary alcohol by zeolite Beta contrasts with the dehydration selectivity shown by smaller pore zeolites, such as ZSM-5, as taught by the prior art.

Zeolite Beta may be composited with a porous matrix material, such as zirconia, silica, titania, alumina, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia. The matrix may be in the form of a cogel. The relative proportions of zeolite component and inorganic oxide gel matrix may vary widely with the zeolite content ranging from between 1 to 99, more usually 5 to 80, percent by weight of the composite.

Any charge stock containing a tertiary alcohol may be used as the feedstock in the process of this invention. Suitable tertiary alcohols include t-butyl alcohol (TBA) and branched $C_5+$ alcohols, such as 2-methyl, 2-butanol. The tertiary alcohol feedstock may contain water and/or hydrocarbons. Useful tertiary alcohol-containing feedstocks include product streams from isobutylene hydration and isobutane oxidation as well as by-product streams from propylene oxide manufacture.

Moderate pressures and relatively low temperatures are important process variables that contribute to high conversion and $C_8$ olefin selectivity. Generally, the temperature is in the range of from about 200° to about 600° F., preferably in the range of from about 200° to about 400° F. At temperatures above about 200° F. dehydration without oligomerization is minimized. At temperatures of less than about 600° F. aromatization is also minimized.

The pressure is generally in the range of greater than about 200 psig, preferably in the range of about 300 to about 1500 psig.

Other conditions such as space velocity are well known parameters and can be optimized for the process herein in the usual manner.

The reactor for alcohol conversion may be of a conventional design well known in the art and it is operated in a conventional manner. A preferred reactor type contains a fixed-bed of catalyst which can be operated in single-pass mode or with product effluent recycle. More than one reactor can be used in series or in parallel.

The following example illustrates the process of the present invention.

EXAMPLE

This example shows the conversion of TBA to olefins over zeolite Beta, prepared in accordance with U.S. Pat. Nos. 3,308,069 and Re. 28,341, incorporated herein by reference. Four runs were conducted. The reaction conditions and feedstock compositions are shown in Table 1. The reaction temperatures ranged from 125°-275° F. The total reactor pressure was 1000 psig for all runs. The TBA feedstock contained a small amount of water and isopropanol to liquefy the normally solid TBA in the feed burets of the pilot unit.

Table 2 shows the conversion and selectivity data. The primary products were identified as $C_8$ and $C_{12}$ olefins, isobutylene and water. The $C_8$ olefins were further characterized by GC/MS (gas chromatography/mass spectrometry) and found to be exclusively the highly branched 2,2,4-trimethyl pentene (TMP) isomers, 2,2,4-trimethyl pentene-1 and 2,2,4-trimethyl pentene-2. At 275° F. in Run 3, where 99% TBA conversion is observed, 70% of the hydrocarbon product is trimethyl-pentenes, 27% $C_{12}$ olefins and only 3% isobutylene. The TMP product was removed by distillation and blended into a regular unleaded gasoline basestock at 10 vol% for product property measurements. The TMP was found to blend at 115 RON, 95 MON, 105 (RON+MON)/2, and 0 psi Reid vapor pressure.

TABLE 1

| | Run No. | | | |
|---|---|---|---|---|
| | 1 | 2 | 3 | 4 |
| Reaction Conditions | | | | |
| reactor pressure (psig) | 1000 | 1000 | 1000 | 1000 |
| avg. reactor temp, °F. | 125 | 200 | 275 | 250 |
| oxygen:olefin molar ratio | 1 | 1 | 1 | 1 |
| time on stream, hr. | 17 | 41 | 65 | 89 |
| space velocity (WHSV), hr$^{-1}$ | 0.78 | 0.78 | 1.57 | 1.53 |
| space velocity (LHSV), hr$^{-1}$ | 0.57 | 0.57 | 1.15 | 1.12 |
| Feed Composition, wt. % | | | | |
| water | 1.33 | 1.33 | 1.33 | 1.33 |
| 2-propanol | 0.71 | 0.71 | 0.71 | 0.71 |
| t-butyl alcohol | 97.96 | 97.96 | 97.96 | 97.96 |

TABLE 2

| Product Composition, wt. % | | | | |
|---|---|---|---|---|
| water | 2.46 | 7.79 | 24.21 | 18.63 |
| 2-propanol | 2.96 | 0.65 | 0.44 | 0.36 |
| t-butyl alcohol | 90.60 | 74.39 | 0.98 | 31.50 |
| isobutylene | 3.43 | 11.26 | 2.22 | 19.05 |
| C$_7$ ether | 0.56 | 0.00 | 0.00 | 0.00 |
| trimethyl pentenes | 0.00 | 5.91 | 52.10 | 27.15 |
| C$_{12}$ olefins | 0.00 | 0.00 | 20.05 | 3.30 |
| Reactant Conversions, wt. % | | | | |
| t-butyl alcohol | 7.52 | 24.06 | 99.00 | 67.84 |
| Hydrocarbon Product Selectivities | | | | |
| isobutylene | 100.0 | 65.6 | 3.0 | 38.5 |
| trimethyl pentenes | 0.0 | 34.4 | 70.0 | 54.8 |
| C$_{12}$ olefins | 0.0 | 0.0 | 27.0 | 6.7 |

In a further embodiment of the present invention, isobutane is used as a starting material in a two step partial oxidation/dimerization process to yield $C_8+$ olefin products. Isobutane partial oxidation is known technology. See Petrochemicals, P. Wiseman and Ellis Horwood, Ltd, p. 68-72 (1986), incorporated herein by reference. Isobutane is reacted with oxygen at moderate temperature and pressure, generally in the range of from about 200° to about 400° F. and from about 100 to about 1000 psig, without the need of a catalyst to give about 50% i-C$_4$ conversion and about 50/50 selectivity to TBA and t-butyl hydroperoxide (TBHP). These products are then fed to a $C_8+$ olefin reactor where they are converted to $C_8+$ olefins over a catalyst composition comprising a large-pore, 12-membered ring material. Overall, this process gives higher olefins starting from isobutane and oxygen. Branched $C_5+$ paraffins may also be useful as a starting material in this two step partial oxidation/dimerization process.

In FIG. 1, isobutane and oxygen are fed through line 1 to partial oxidation reactor 2 where they react to form TBA and TBHP which are removed through line 3. Unreacted isobutane and oxygen are recycled back to the partial oxidation reactor 2 through line 4. The TBA and TBHP are fed through line 3 to the $C_8+$ olefin reactor 5 containing a catalyst composition comprising a zeolite having the structure of zeolite Beta 6 where they are converted to $C_8+$ olefin product which is removed through line 7. Unreacted TBA and TBHP are recycled back to the $C_8+$ olefin reactor through line 8. Any isobutane and/or oxygen produced in $C_8+$ olefin reactor 5 is recycled back to the partial oxidation reactor 2 through line 9. In another embodiment of the process, unreacted oxygen is removed and recycled after the partial oxidation reactor 2 through line 4 and unreacted isobutane and TBA and TBHP product are fed through line 3 to the $C_8+$ olefin reactor 5.

Another advantage of the process of the present invention is the ability to produce high octane blending stocks by conversion of TBA can extend the options available to refiners to increase the yields of high octane components from less valuable starting materials. A further advantage of the process of the present invention is the two step process converting isobutane to $C_8+$ olefins can be practiced in a refinery or in a chemical plant, for example, in a chemical plant involved with propylene oxide manufacture.

Changes and modifications in the specifically described embodiments can be carried out without departing from the scope of the invention which is intended to be limited only by the scope of the appended claims.

I claim:

1. A process for the conversion of a tertiary alcohol feedstock to $C_8+$ olefins which comprises contacting said tertiary alcohol feedstock with a catalyst composition comprising a large-pore, 12-membered ring material at a sufficient temperature and pressure to convert said tertiary alcohol feedstock to $C_8+$ olefin products.

2. The process of claim 1 in wherein said contacting is at a temperature in the range of from about 200° F. to about 600° F.

3. The process of claim 1 wherein said contacting is at a pressure of greater than about 200 psig.

4. The process of claim 1 wherein said catalyst composition comprises a zeolite having the structure of zeolite Beta.

5. The process of claim 1 wherein said catalyst composition comprises a zeolite having the structure of zeolite Y.

6. The process of claim 1 wherein said catalyst composition comprises a zeolite having the structure of mordenite.

7. The process of claim 1 wherein said tertiary alcohol feedstock comprises t-butyl alcohol.

8. The process of claim 1 wherein said temperature is in the range of from about 200° to about 400° F.

9. The process of claim 1 wherein said $C_8+$ olefin products comprise 2,2,4-trimethyl pentene.

10. The process of claim 1 wherein said tertiary alcohol feedstock comprises branched $C_5+$ alcohols.

11. The process of claim 1 wherein said tertiary alcohol feedstock comprises water.

12. The process of claim 1 wherein said tertiary alcohol feedstock further comprises isobutane and/or t-butyl hydroperoxide.

13. A process for the conversion of a t-butyl alcohol feedstock to $C_8+$ olefin products which comprises contacting said t-butyl alcohol feedstock with a catalyst composition comprising a zeolite having the structure of zeolite Beta at a temperature in the range of from about 200° to about 600° F. and a pressure of greater than about 200 psig.

14. The process of claim 13 wherein said temperature is in the range of from about 200° to about 400° F.

15. The process of claim 13 wherein said $C_8+$ olefin products comprise 2,2,4-trimethyl pentene.

16. A process for the conversion of t-butyl alcohol to $C_8+$ olefin products which comprises:
    contacting isobutane with oxygen in a first step to convert said isobutane to a partial oxidation product comprising t-butyl alcohol; and
    contacting said partial oxidation product comprising t-butyl alcohol with a catalyst composition comprising a large-pore, 12-membered ring material in a second step at a sufficient temperature and pressure to convert said t-butyl alcohol to said $C_8+$ olefin products.

17. The process of claim 16 wherein said catalyst composition comprises a zeolite having the structure of zeolite Beta.

18. The process of claim 16 wherein said $C_8+$ olefin products comprises 2,2,4-trimethyl pentene.

19. The process of claim 16 wherein said partial oxidation product comprises unreacted isobutane and/or t-butyl hydroperoxide.

20. The process of claim 16 wherein said second step is carried out at a temperature in the range of from about 200° to about 600° F.

21. The process of claim 16 wherein said second step is carried out at a temperature in the range of from about 200° to about 400° F.

22. The process of claim 16 wherein said second step is carried out at a pressure of greater than about 200 psig.

* * * * *

UNITED STATES PATENT AND TRADEMARK OFFICE
CERTIFICATE OF CORRECTION

PATENT NO. :     5,157,192
DATED      :
INVENTOR(S) :    October 20, 1992
                 C.M. Sorensen It is certified that error appears in the above-identified patent and that said Letters Patent is hereby corrected as shown below:

Col. 4, claim 1          "olefins" should be
     line 44              --olefin products--

Signed and Sealed this

Twelfth Day of October, 1993

Attest:

BRUCE LEHMAN

*Attesting Officer*          *Commissioner of Patents and Trademarks*